United States Patent [19]

Grill, Jr. et al.

[11] Patent Number: 5,505,201
[45] Date of Patent: Apr. 9, 1996

[54] IMPLANTABLE HELICAL SPIRAL CUFF ELECTRODE

[75] Inventors: Warren M. Grill, Jr.; Matthew D. Tarler, both of Cleveland Heights; John T. Mortimer, Chagrin Falls, all of Ohio

[73] Assignee: Case Western Reserve University, Cleveland, Ohio

[21] Appl. No.: 230,342

[22] Filed: Apr. 20, 1994

[51] Int. Cl.$^6$ .................... A61B 5/04; A61N 1/05
[52] U.S. Cl. ........................ 128/642; 607/118
[58] Field of Search ................... 607/118, 116, 607/117, 149, 152; 128/642

[56] References Cited

U.S. PATENT DOCUMENTS

| | | | |
|---|---|---|---|
| 4,133,735 | 1/1979 | Afromowitz et al. | |
| 4,573,481 | 3/1986 | Bullara | 607/118 |
| 4,590,946 | 5/1986 | Loeb | |
| 4,602,624 | 7/1986 | Naples et al. | |
| 4,608,985 | 9/1986 | Crish et al. | |
| 4,628,942 | 12/1986 | Sweeney et al. | |
| 4,649,936 | 3/1987 | Ungar et al. | |
| 4,837,049 | 6/1989 | Byers et al. | |
| 4,903,702 | 2/1990 | Putz | |
| 4,920,979 | 5/1990 | Bullara | 607/118 |
| 4,979,511 | 12/1990 | Terry, Jr. | 607/118 |
| 5,074,313 | 12/1991 | Dahl et al. | |
| 5,143,067 | 9/1992 | Rise et al. | 607/118 |
| 5,199,430 | 4/1993 | Fang et al. | |
| 5,215,089 | 6/1993 | Baker, Jr. | 607/118 |
| 5,251,634 | 10/1993 | Weinberg | 607/117 |
| 5,324,322 | 6/1994 | Grill, Jr. et al. | 607/118 |
| 5,344,438 | 9/1994 | Testerman et al. | 607/118 |

FOREIGN PATENT DOCUMENTS

| | | |
|---|---|---|
| 2195897 | 4/1988 | United Kingdom. |
| WO93/20887 | 10/1993 | WIPO. |

OTHER PUBLICATIONS

IEEE Transactions on Biomedical Engineering, "A Spiral Nerve Cuff Electrode for Peripheral Nerve", vol. 35, No. 11, Nov. 1988.

*Primary Examiner*—Lee S. Cohen
*Attorney, Agent, or Firm*—Fay, Sharpe, Beall, Fagan, Minnich & McKee

[57] ABSTRACT

A self-curling elongate non-conductive sheet (A) defines a helical cuff electrode (10). A plurality of contact members (40) are linearly disposed along a direction (C) between a first layer (30) and a second layer (32) of laminated elastomeric material. The first layer is stretched along direction (F) oblique to the direction (C) before lamination such that the cuff electrode is elastomerically biased to curl into a helix. Windows (50) are defined in the elastomeric first layer (31) and bonding layer (34) to provide for electrical conduction between the contact members (40) and the nerve tissue (60) about which the cuff is wrapped. Method steps for endoscopic implantation of the cuff electrode (10) include flattening and then sliding the cuff from a carrier (100), the cuff helically self-wrapping around the nerve as it is urged from the carrier held stationary.

25 Claims, 4 Drawing Sheets

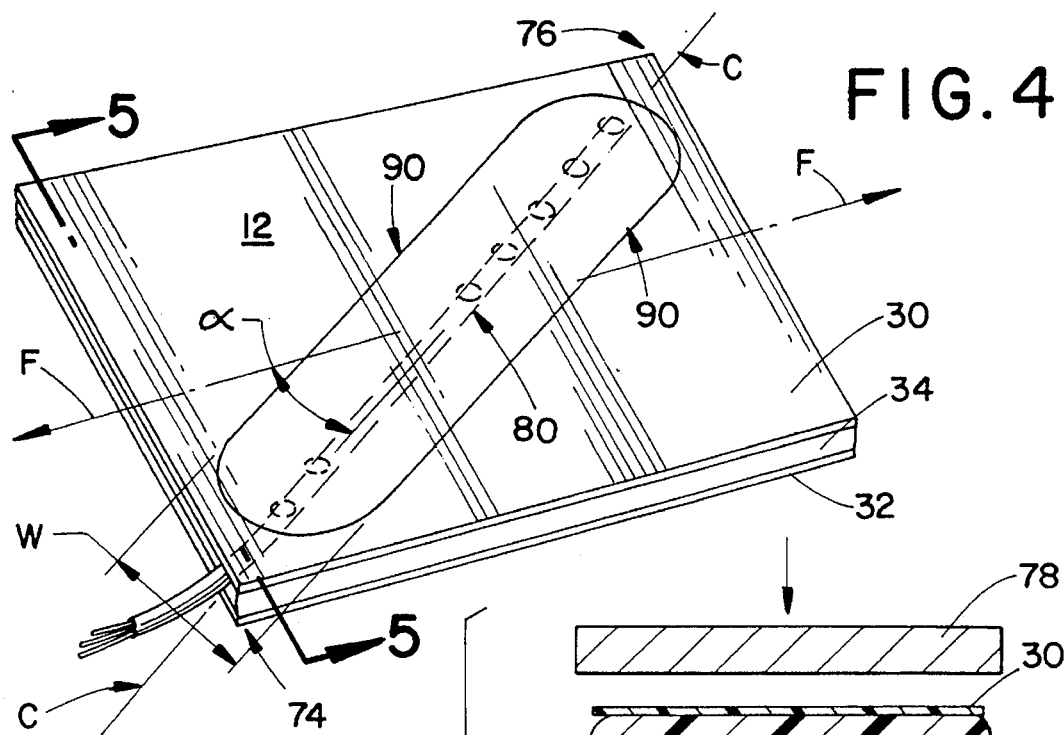
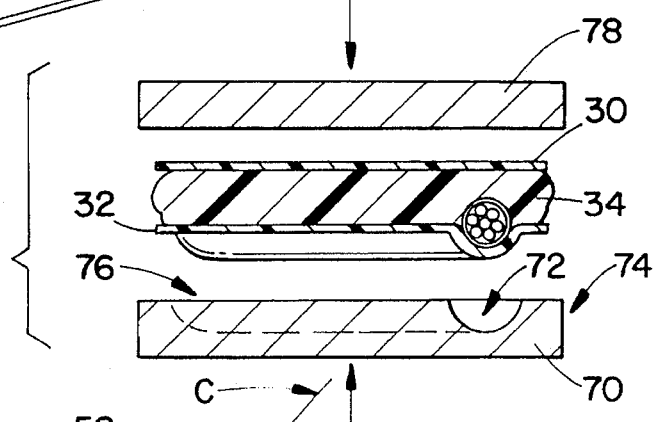
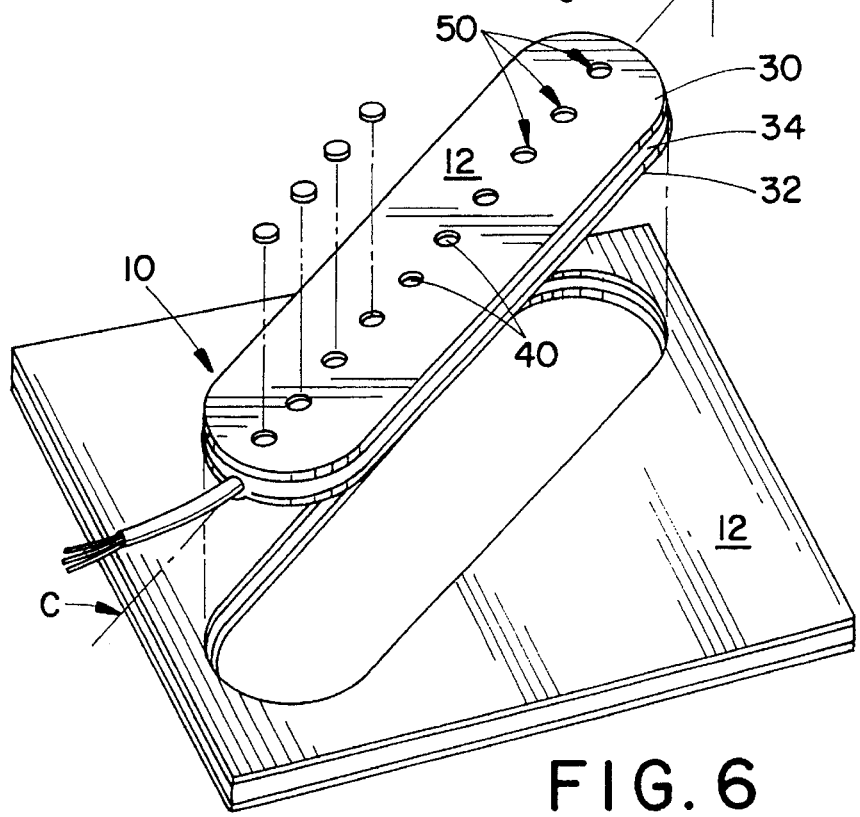

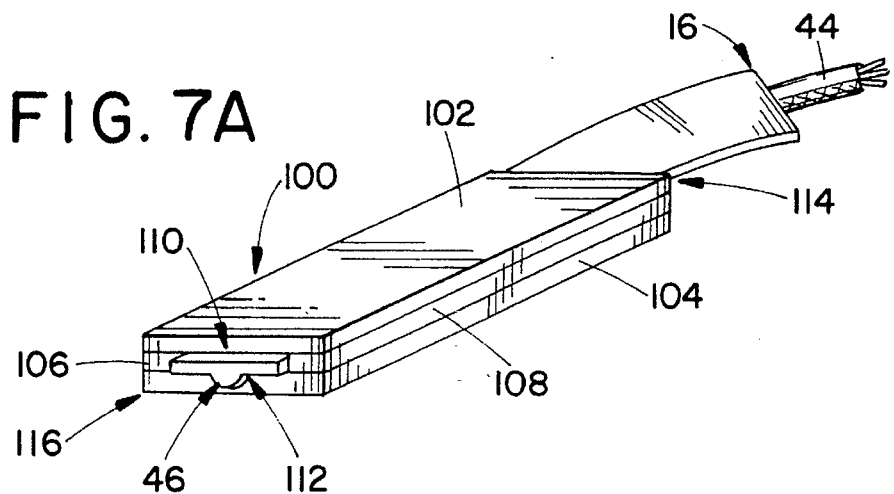
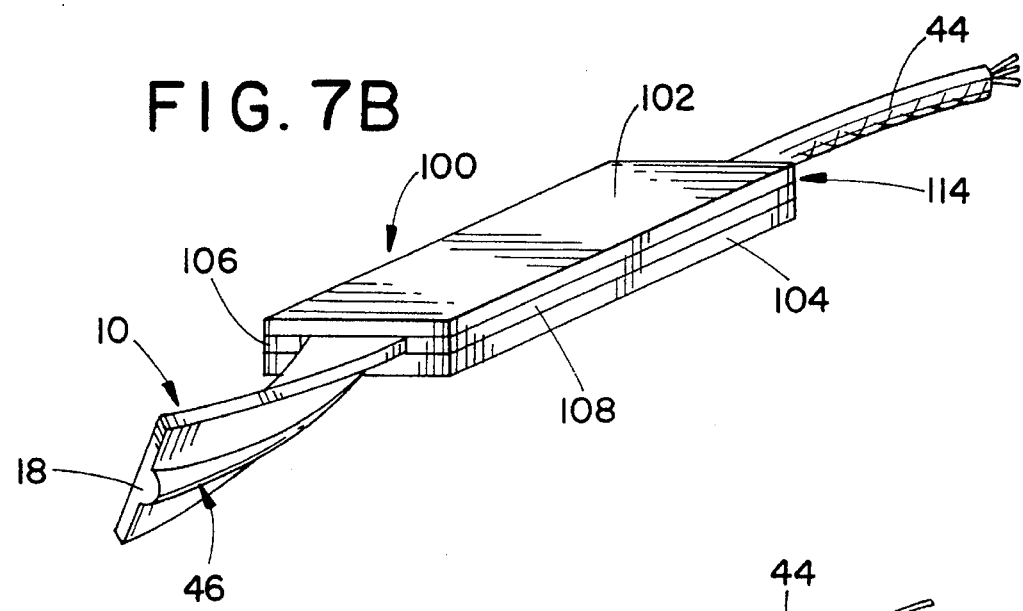

IMPLANTABLE HELICAL SPIRAL CUFF ELECTRODE

CROSS-REFERENCE TO RELATED APPLICATION

Cross-reference is made to our earlier application Ser. No. 07/871,352 filed Apr. 20, 1992, now U.S. Pat. No. 5,324,322 the teachings of which are incorporated herein by reference.

BACKGROUND OF THE INVENTION

The present invention relates to the biomedical arts, and in particular to implantable electrodes, their manufacture and surgical endoscopic installation. The present invention finds particular application in conjunction with cuff electrodes which are self-biased to helically curl around and snugly engage a nerve trunk, and will be described with particular reference thereto. It is to be appreciated, however, that the invention is also applicable to other types of implanted biomedical devices for introducing, monitoring, or removing matter or energy by helical engagement with body tissue.

Electrical activation of the nervous system has been shown in recent years to offer great hope in restoring some degree of lost sensory and motor function in stroke victims and individuals with spinal cord lesions. Ways in which electrical activation of the nervous system can be utilized to restore a particular function include: (1) the use of surface electrodes to activate the nerves in the general region of interest; (2) the use of intramuscular electrodes, also to activate the nerves in a general region; and, (3) the use of nerve cuff electrodes placed around specific nerves of interest and used to activate them specifically and singularly. The third alternative offers advantages over the first two in that it requires the least amount of stimulating current and hence a minimal amount of charge injected into the tissue. In addition, it allows easy excitation of entire muscles rather than merely parts of muscles, a common situation for the first two categories. Because the use of nerve cuff electrodes requires delicate surgery, they are usually contemplated only when excitation of specific, isolated muscles is desired or the generation of unidirectional action potentials is required.

One prior art cuff electrode includes a cylinder of dielectric material defining a bore therethrough of sufficient diameter to receive the nerve trunk to be electrically stimulated. The cylinder has a longitudinal split or opening to facilitate spreading the cuff open in order to receive a nerve therein. After installation, the longitudinal split is sutured or otherwise held closed. Although suturing holds the cuff in place, an electric current path is defined through the split which permits current leakage. Two or three annular electrodes are positioned on the inner surface of the bore for use in applying the electrical stimuli. The electric stimuli may be used to generate propagating nerve impulses or may be used to block naturally occurring nerve pulses traveling along the nerve trunk, or the like.

Another earlier nerve cuff electrode described in U.S. Pat. No. 4,602,624 encircles a nerve trunk or other body tissue with at least one medication or electrical energy conductive member held against the tissue and a non-conductive sleeve extending to either side of the conductive member. This earlier cuff is cylindrical and includes a self-curling sheet of non-conductive material which is self-biased to curl into a tight overlapping cylindrical spiral or roll around the nerve trunk. At least one conductive member is disposed adjacent an edge of the self-curling sheet. To install the above-described cuff, the self-curling sheet is held flat with the conductive member adjacent the body tissue to receive the cuff. Thereafter, the self-curling sheet is permitted to curl into a tubular spiral or cylinder around the body tissue in an overlapping fashion. Accordingly, this cuff electrode can be difficult to implant where access completely around the nerve is limited. Also, this earlier cuff is essentially inflexible axially.

U.S. Pat. No. 4,590,946 to Loeb describes a surgically implantable electrode system which includes two or more electrically conductive elements embedded in a helically wound substrate made of insulative material. The preferred substrate is a bio-compatible polymer material such as silicone rubber, having sufficient stiffness to maintain its helical shape during the surgical manipulations necessary to position the electrode around a nerve bundle. The substrate is pre-shaped or molded defining its overall spiral contour and open space within the helix, and thus cannot be fabricated in a planar configuration. A separate membrane pouch is needed to insulate the electrode from the adjacent body tissue. This pouch greatly increases the bulk of the electrode and thus increases the potential for mechanically induced neural trauma. Also, the lead-in conductors must be anchored by a strain relief. This being the case, the Loeb electrode is difficult to manufacture, somewhat stiff axially and hard to implant.

The open helix of the Loeb electrode requires the additional insulating membrane pouch to exclude current flow without, or include flow within, the pouch. The cuff electrode of the present invention is manufactured in a closed helix form which does not require an external pouch to control current flow.

Because of its stiffness, the Loeb electrode requires a turning or "threading" of the electrode onto a nerve for implantation and thus necessitates an open surgical procedure. The cuff electrode of the present invention is "self turning" or "self threading" when used in conjunction with a specialized installation tool and therefore does not require an open surgical procedure for implantation.

Lastly, the Loeb electrode requires molding during its fabrication and thus cannot be manufactured in a planar configuration. The electrode of the present invention, however, is fabricated in a planar configuration and then formed into a three dimensional structure as a result of its inherent self-biasing. Planar fabrication is an advantage because it allows thin-film production techniques to be employed as described in our pending patent application Ser. No. 07/871,352.

The present invention contemplates a new and improved helical cuff electrode which is readily installed and removed with minimum surgery and without damaging the nerve trunk or other tissue. The present invention further contemplates a method of cuff manufacture and endoscopic installation tools and methods.

SUMMARY OF THE INVENTION

In accordance with the present invention, a helical nerve cuff electrode is provided for encircling a nerve trunk or other body tissue with at least one medication or electrically energy conductive member disposed along the length of the helical cuff. The cuff includes a self-curling sheet of non-conductive material laminations which are collectively self-biased to curl into a tight helix.

In accordance with another aspect of the present invention, a cuff electrode is provided including a plurality of stimulating and/or recording contact surfaces, leads for making connection to the contacts from outside of the cuff electrode and a biased or pre-stressed polymer substrate. The substrate curls into a helical spiral around nerve fibers or other body tissues as it relaxes.

In accordance with yet another aspect of the invention, a cuff electrode is manufactured or otherwise fabricated by bonding one or more stressed polymer layer(s) to one or more unstressed polymer layer(s), the contacts and leads being disposed therebetween. Thereafter, the cuff is cut from the stressed and unstressed polymer laminate at an angle oblique to the direction of the original initial stress.

In accordance with still yet another aspect of the invention, the self-curling helical cuff electrode of the above-described construction is held flat prior to installation over the nerve by a specialized tool having an elongate hollow center portion matching the exterior dimensions of the cuff. The first end of the self-curling helical cuff is ejected from the specialized tool by sliding and held against the body tissue intended to receive the cuff. Thereafter, the free end of the self-curling cuff is permitted to curl into a helical form around the body tissue as the electrode is urged from the carrier tool. Installation is complete when the cuff electrode is completely advanced from the tool and onto the target nerve.

A primary advantage of the present invention is that it is easily installed on and removed from a nerve or other body tissue. Another advantage is that a plurality of stimulation and sampling points for inducting and recording nerve activity, respectively, are accomodatable both longitudinally and circumferentially around the nerve trunk. A further advantage of the present invention is that the helical contour and self-curling propensity of the cuff compensates for variations and expansion in the diameter of the nerve and surrounding tissue. As the tissue may expand, so too does the cuff freely.

Another advantage of the present invention is that although the cuff electrode is fabricated in a planar, two dimensional configuration, a three dimensional cuff results as the corporate configuration is permitted to relax into its final helical spiral contour.

A further advantage of the present invention is that although during manufacture all electrode contacts for stimulation and/or recording lie along a single trace line, after curling of the cuff, the contacts can be positioned anywhere on the surface of the target nerve trunk. This permits control over both longitudinal and circumferential contact placement.

Still yet a further advantage of the present invention is that a tool is provided in combination with the electrode for easily installing the helical nerve cuff around the target body tissue using endoscopic procedures.

Still further advantages of the present invention will become apparent to those of ordinary skill in the art upon reading and understanding of the following detailed description of the preferred embodiments.

BRIEF DESCRIPTION OF THE DRAWINGS

The invention may take form in various parts and arrangements of parts or in various steps and arrangements of steps. The figures and the described structures and methods are only for purposes of illustrating the preferred embodiments of the invention and are not to be construed as limiting same.

FIG. 4 is a perspective view of a step in the process of manufacture of the cuff electrode of FIG. 1;

FIG. 5 is a sectional view through section 5—5 of FIG. 4 and including additional apparatus to illustrate another step in the manufacture of the cuff electrode of FIG. 1;

FIG. 6 is a perspective view of yet another step in the manufacture of the cuff electrode of FIG. 1;

FIGS. 7A–7C are perspective views of a method and apparatus for installing the cuff electrode of FIG. 1 onto a target body tissue; and, FIGS. 8A–8C are perspective views of another method and apparatus using fluid or gas ejection to install the cuff electrode of FIG. 1 onto a target body tissue.

DETAILED DESCRIPTION OF THE PREFERRED EMBODIMENTS

Figure 1:
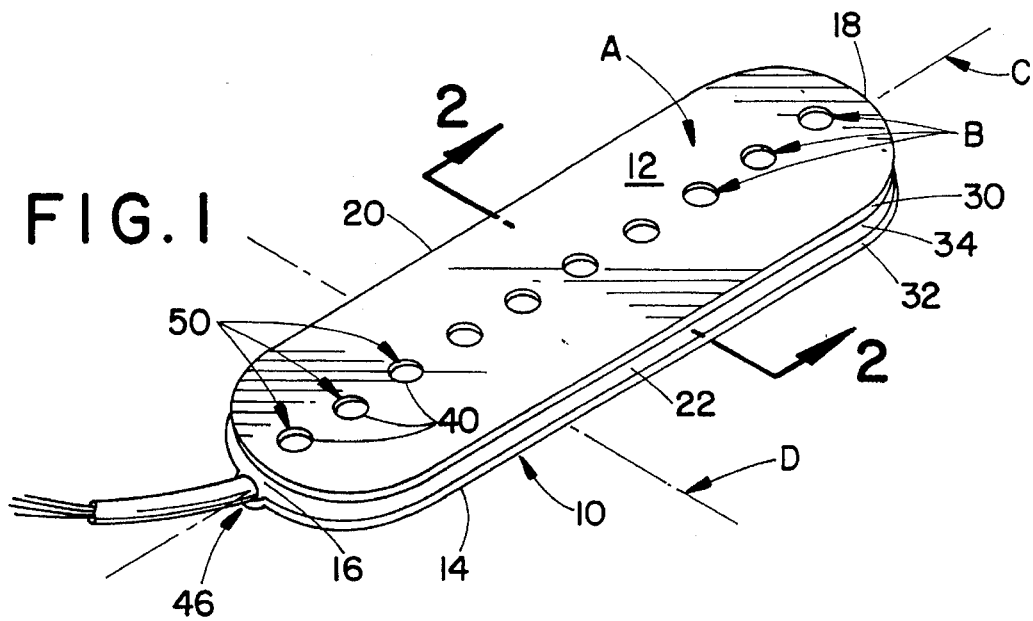
FIG. 1 is a perspective view of a helical self-curling nerve cuff electrode in accordance with the present invention constrained to a generally flat, uncurled configuration.
Figure 2:
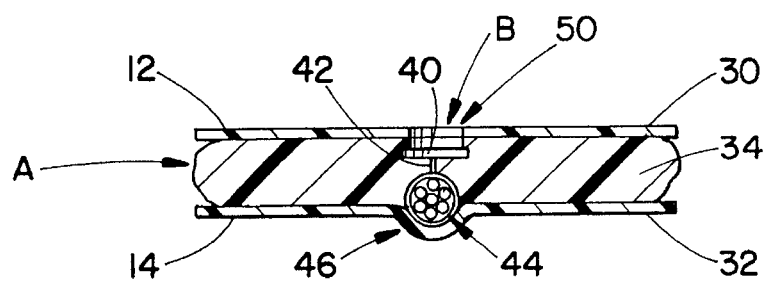
FIG. 2 is a sectional view through section 2—2 of FIG. 1.

With reference to FIGS. 1 and 2, an implantable nerve cuff electrode 10 includes a self-curling non-conductive elongate sheet A to which one or more conductive segments or contacts B are attached or embedded. The self-curling sheet defines a longitudinal or major axis C and a lateral or minor axis D perpendicular to the major axis. The sheet is self-biased or otherwise pre-stressed to curl into a tubular helix as illustrated best in FIG. 3.

Referring still to FIGS. 1 and 2, however, the self-curling sheet A includes a first generally planar surface 12 and an oppositely disposed second generally planar surface 14. Preferably, the self-curling sheet is generally rectangular and extends from a first edge 16 to an oppositely disposed second edge 18 and from a first end 20 to an oppositely disposed second end 22.

In the preferred embodiment, the self-curling sheet is self-biased to curl into a helix by a first layer 30 and a second layer 32 of dissimilar size. The first and second layers 30, 32 are separated by an interstitial flexible bonding layer 34. As described in greater detail below, the first layer 30 is an elastomeric material which is stretched obliquely with respect to both the major and minor axes C, D of the cuff electrode 10 before it is laminated to the second layer 32. In this way, when the first layer is relaxed, it tries to contract but the second layer holds, through the bonding layer, the adjoining surface stretched.

More particularly, the first surface 12 contracts smaller than the second surface 14 in a direction oblique with respect to the major axis C of the cuff electrode causing the elongate sheet A to curl into a helix. The direction and magnitude of the off-axis contractive forces of the first layer define the resultant helical characteristics of the cuff in a manner described more particularly below. In the preferred embodiment, both the first and second layers are non-conductive flexible polymers adhered together by a bonding layer 34 such as silicone rubber, epoxy of the like although silicon rubber type MDX4-4210 is preferred and has been found to be particularly well suited for this application. The layers may be initially assembled uncured then later air cured, temperature cured, vulcanized or the like after fabrication.

Other bio-compatible materials are contemplated. For example, the stretchable first sheet 30 may be cured silicon rubber and the second sheet 32 may be TEFLON film, a platinum mesh, or other bio-compatible sheets. As yet another alternative, the stretched first layer may also be any non-rubber polymeric material which is both bio-compatible and evidences appropriate elastomeric properties to cause a stress sufficient to produce the required bias to induce the self-curling feature. It is to be appreciated that the thickness and overall dimensions of the layers are exaggerated in the figures for clarity and ease of reference for the instant discussion.

In the preferred embodiment, the conductive segments B are disposed between the first and second layers 30, 32 and within the bonding layer 34. With particular reference to FIG. 2, each of the plurality of conductive segments B includes a metal foil contact member 40 bonded to a single electrically conductive lead 42. The collection of leads form a bundle 44 of electrical lead wires extending from the first edge 16 of the cuff electrode 10. The contact members 40 may be formed of platinum, platinum iridium, stainless steel, titanium or iridium/iridium oxide.

The bonding of the contacts 40 to the leads 42 is preferably accomplished by welding although other processes may be employed such as soldering or gluing through use of conductive epoxies or the like. The leads 42 are multi-stranded stainless steel wires or other electrically conductive materials having suitable compliance to permit curling and flexion, having low electrical resistance and good bio-compatible properties. Other materials may be used such as platinum iridium or similar materials. Each of the leads 42 are coated with an insulating material such as TEFLON or silicone rubber so as to be electrically isolated within the length of the cuff and beyond. Contact members 40 are thereby electrically isolated and, therefore, separately excitable or provide separate detectable signals. Also, although the contacts are illustrated as discrete dots or points which engage the nerve at discrete locations, they may be bands or strips or other configurations to helically encircle the nerve. Furthermore, the bands or strips may be oriented such that they form a circle around the nerve, rather than a helical shape, when the cuff is installed. Additionally, although the contacts in the FIGURES are positioned in a linear array, they may be offset laterally to position them on other regions of the nerve trunk.

Still further, the preferred contact members and associated hardware are electrically conductive but may be substituted with fluid conductive members and apparatus for medication infusion and/or fluid sampling or collection. Also, some of the conductive members may be electrically conductive while others are fluid conductive within a single cuff electrode for mixed electrical and fluid exchanges.

The inner or first surface 12 includes a plurality of windows 50 which are cut-outs defining openings to provide direct electrical access to each of the contact members 40. The windows 50 are selectively placed in the first surface 12 and are suitable sized to completely expose an appropriately-sized surface of the contact members to the target nerve or other body tissue. Although the preferred embodiment has been described above as including separate discrete metal foil contact members 40, electrical contact with the target nerve can be established by selectively removing small amounts of the insulation along the length of the leads 42 and defining windows 50 along the cuff where the insulation is removed. Also, the leads and/or contact members may be fabricated using thin metallic film technology by chemical or physical vapor deposition as demonstrated in our earlier co-pending application Ser. No. 07/871,352 filed Apr. 20, 1992.

Figure 3:
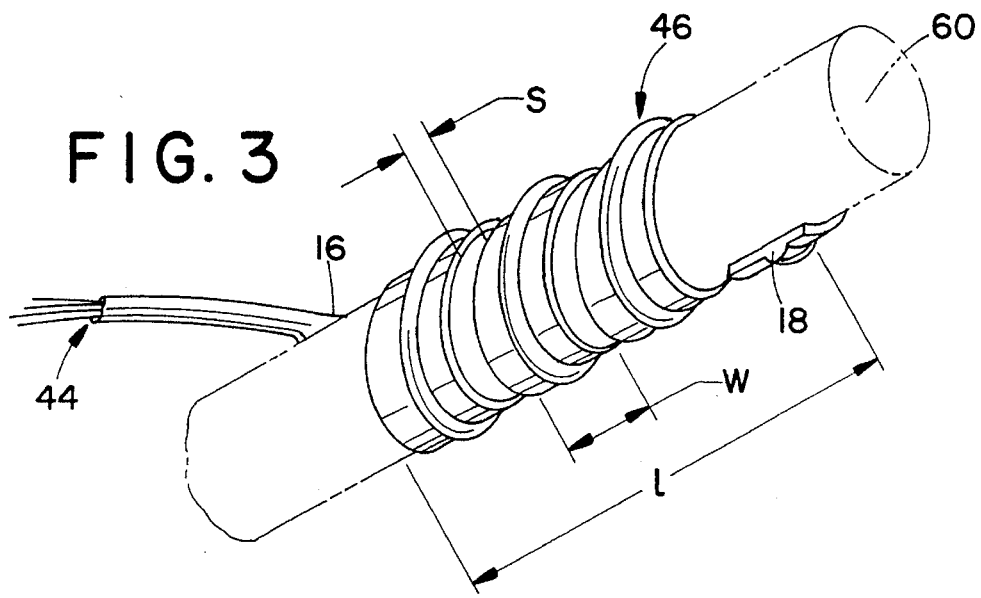
FIG. 3 is a perspective view of the cuff of FIG. 1 disposed in a helical configuration around a body tissue fiber.

The aggregate collection of wires comprising the lead wire bundle 44 forms a spine 46 on the second surface 14 of the electrode 10. The spine 46 is advantageously positioned on the "outside" of the helix as best illustrated in FIG. 3 wherein the electrode 10 is shown placed over a nerve trunk 60 or other biological tissue for stimulation or recording of electrical signals. The windows 50 and the contact members 40 exposed through the windows lie on the "inside" of the helix and are thus not visible in FIG. 3. The spine itself, as well as its placement with respect to the remainder of the cuff, enhances the physical integrity of the cuff electrode 10 in both the longitudinal and circumferential directions with respect to the elongate nerve or body tissue 60. Cuff fabrication with the spine on the outside of the helix permits the contact members 40 to lie in close proximity to the target tissue 60 for maximum efficiency of electrical and/or chemical signal exchange.

With continued reference to FIG. 3, the general physical features of the helical pattern assumed by the cuff electrode 10 may be described using three (3) basic parameters. These include the width w of the electrode 10, the spacing s between successive turns of the helical electrode around the nerve and the overall length 1 of the electrode in close wrapped contact with the nerve 60. All three (3) of these parameters are selectable either during the manufacturing process or during the process of surgical endoscopic installation. However, the thickness of the nerve itself influences at least the spacing s and the length 1 parameters. Also, in general, the spacing s between successive wraps of the electrode is dependent on the pitch of the helical shape of the electrode. The pitch in turn depends in part on the inherent dissimilarity in resting or relaxed size between the first and second surfaces 12, 14 built-in during fabrication in a manner described below.

An exemplary method of cuff electrode manufacture will now be described with particular reference to FIGS. 4–6. To begin, a first sheet of cured silicone elastomer 30 having a thickness of 0.005 inches is fixed at opposite ends by clamps. Sheets of other thicknesses can also be used. The sheet is then stretched in a direction F across a steel plate, six (6) inches long. The length of the exposed sheeting between the clamps in the unstretched state is varied according to the final diameter and desired pitch of the helical cuff electrode. A shorter length of unstretched sheeting results in a greater amount of stretch and a smaller final cuff diameter and/or a cuff having a smaller pitch (i.e. tighter wrapped helix). If the stretch is increased enough and the nerve trunk thin enough, the various wraps of the helix will overlap each other.

Although the sheet is being stretched in the direction F in the FIGURE, it may be alternatively stretched along an axis which is perpendicular to the direction F. Still yet, combinations of stretching directions and axes are contemplated according to these teachings in order to achieve a cuff electrode having a deemed final configuration.

The next step is to secure a second rectangular sheet of cured silicone elastomer 32 to a first molding plate 70. The plate 70 preferably includes an oblique groove 72 disposed therein. The groove 72 extends uninterrupted from a first corner 74 of the plate 70 to an opposite and second corner 76. The second layer 32 is not stretched on the plate 70. Rather, a completed contact assembly 80 is placed upon the second layer. The contact assembly is disposed along the second layer to define a longitudinal axis C matching that of the groove 72 as illustrated in best FIGS. 4 and 6.

Next, a liquid elastomeric bonding material 34, preferably silicone rubber MDX4-4210, is spread over the contact assembly completely covering the contact members, leads and the unstretched bottom sheet 32. The stretched first elastomeric sheet 30 is brought into contact with the adhesive 34 and compressed by a second molding plate 78. The second plate 78 maintains pressure on the layered assembly throughout the curing process of the adhesive 34. This not only assures that the flowable adhesive completely fills all voids in the contact assembly 80, but also guarantees that the resultant cuff electrode is of minimum and uniform thickness.

After the liquid elastomeric bonding material 34 is cured, the upper plate 78 is removed exposing the first surface 12 of the laminated assembly including the cuff electrode 10 shown in outline form in FIG. 4. The first surface forms the inside of the helix held against the nerve. As illustrated best in FIG. 6, a plurality of windows 50 are cut from the first stretched layer 30 as well as from the adhesive layer 34 as necessary to expose the metal foil contact members 40.

As a final step, the cuff electrode itself is cut from the rectangular layered assembly along the pattern lines 90 illustrated best in FIG. 4. Each of the first, second and adhesive layers 30, 32 and 34 respectively are cut completely through for easy removal of the electrode 10 as shown in FIG. 6. The layered assembly surrounding the lead bundle 44 is trimmed away as necessary. Once removed from the layered assembly, the electrode 10 springs naturally into the helix illustrated best in FIG. 3.

As indicated above, the longitudinal or major axis C (FIG. 1) is oblique with respect to the force F (FIG. 4) applied along the basic orthoganal axes of both the first and second rectangular layers 30, 32 forming the laminated construction. The orthoganality of off-axis pitch α of the major axis C is carefully selected based upon the compositions of the first and second layers, the stretch force exerted upon the first sheet and the final desired helical cuff electrode configuration or orientation.

To obtain a close or "tight" helix (i.e. s=0) α is calculated from the desired width w of each wrap and the desired circumference c of the cuff electrode according to the relation:

$$\alpha = \arctan\left[\frac{w}{c}\right]$$

The spacing s between adjacent wraps of the cuff electrode is controlled by altering the angle α between the direction of stretch and the longitudinal axis c. Increasing values of α result in electrodes having a progressively more open helix while decreasing values of α eventually result in electrodes having an overlap between adjacent wraps of the cuff electrode. The circumference c of the resulting cuff is controlled by altering the degree of stress imposed on the stretched first sheet 30.

The preferred method of installing the cuff electrode discussed above includes the use of specialized electrode carrier 100 illustrated in FIGS. 7A–7C. With reference now to those figures, the carrier 100 includes a pair of spaced apart planar members 102, 104 defining a top and bottom of the carrier respectively. The planar members are held in their spaced apart relationship by a pair of longitudinal guide members 106, 108 which are particularly sized to separate the planar members 102, 104 by an amount sufficient to accommodate the thickness of the preferred cuff electrode 10 described above. The planar members 102, 104 spaced apart by the longitudinal guide members 106, 108 define a channel 110 adapted for slidably receiving the cuff electrode 10 therein.

The lower or bottom planar member 104 includes a groove 112 which extends uninterruptedly longitudinally from an entrance end 114 of the electrode carrier 100 to the exit end 116 thereof. The groove 112 is suitably sized to accommodate the spine 46 of the cuff electrode 10. Lastly, the planar members 102, 104 are preferably snap-fitted to the longitudinal guide members 106, 108 for easy assembly and disassembly during or prior to surgical endoscopic implantation of the cuff electrode 10.

To use the electrode carrier 100, the second edge 18 of the cuff electrode 10 is inserted into the entrance end 114 of the channel 110. The electrode, originally in its relaxed and helical shape in constrained by the close fit of the channel 110 into a flat or uncurled state as best illustrated in FIG. 7A. Referring to particularly to that FIGURE, the cuff electrode 10 is held entirely within the channel 110 of the electrode carrier 100 with just a small amount of the second edge 18 extending therefrom. The first edge 16 extends from the entrance end 114 of the carrier 100. The spine 46 is positioned in the groove 112.

Figure 8A:
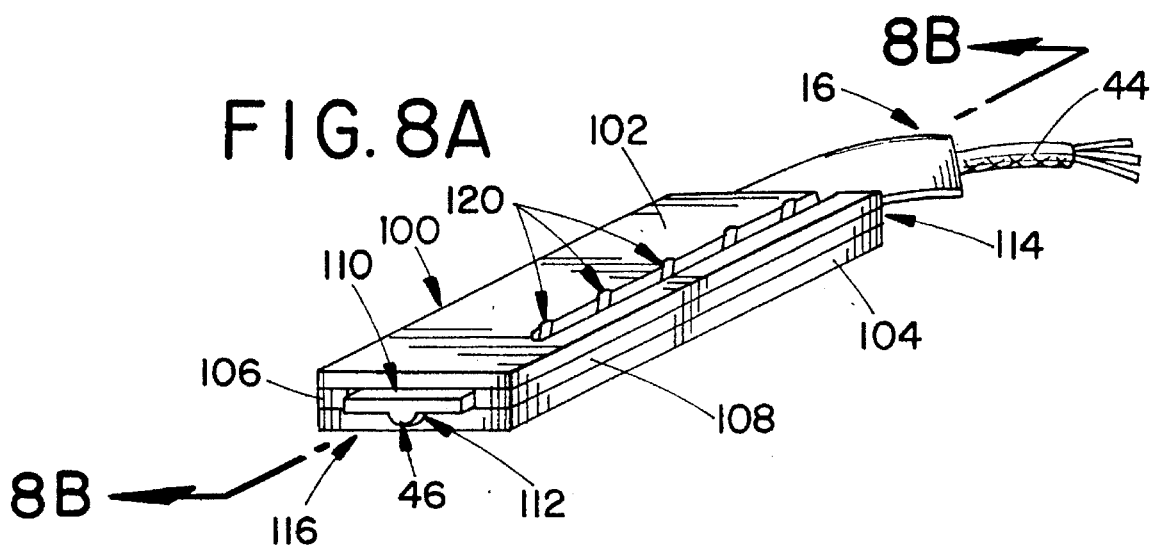
Figure 8B:
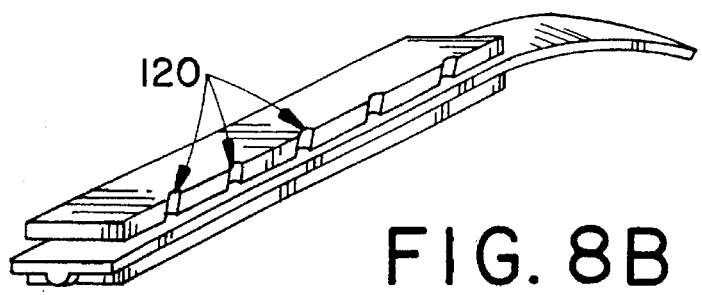
Figure 8C:
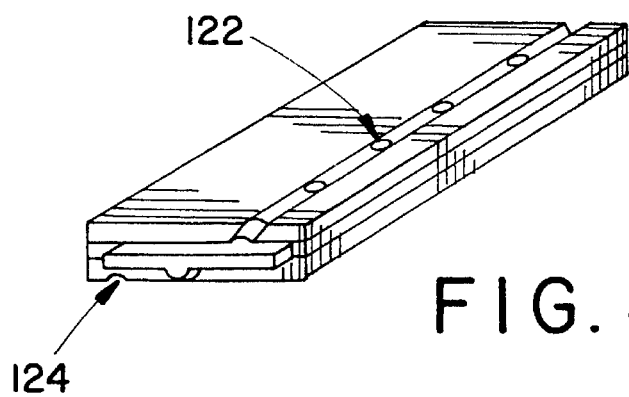

By manually pushing on the electrode within the electrode carrier or on the lead bundle 44 extending from the entrance end 114 of the electrode carrier 100, the cuff electrode 10 is advanced from the exit end 116 of the carrier 100 as best illustrated in FIG. 7B. Another method of pushing the electrode from the carrier 100 involves using pressurized liquid or gas injected into ports 120 provided in the carrier as illustrated in FIGS. 8A–8C. Pressurized fluid escaping through the ports 120 push surfaces 12 and 14 of the cuff in a downward and outward in a manner to advance the cuff towards the exit end 116 as illustrated in FIG. 7B. The pitch of the parts (FIG. 8B) as well as the rate of fluid injected through the parts determines the rate of advancement of the electrode. This preferred method of advancement could also be substituted by a number of mechanical means including but not limited to rollers, slides or plungers formed or placed on or in the carrier 100. FIG. 8C illustrates an embodiment including an opposing pair 122, 124 of vent parts 120 for simultaneous top and bottom urging the electrode from the carrier. In this manner, an "air bearing" is created for reducing the friction between the cuff electrode and the carrier.

As the electrode exits the carrier, the free end relaxes into its helical or pre-stressed orientation. This relaxation partially along the length of the cuff electrode is advantageously used to wrap the electrode around the nerve trunk or other biological tissue (not shown). The cuff electrode 10 and carrier 100 thus combine for easy endoscopic implantation. In the position illustrated in FIG. 7B, the leading edge 18 of the electrode 10 is placed adjacent or below the nerve targeted for the implant.

As the electrode is further advanced from out of the carrier 100, it automatically wraps around the nerve (not shown) by relaxing into an equilibrium helical shape or configuration as best illustrated in FIG. 7C. After the electrode is completely urged out from the carrier, the top planar member 102 is snapped open exposing the bundle 44 and freeing the carrier 100 for removal.

The invention has been described with reference to the preferred embodiments. Obviously, modifications and alterations will occur to others upon reading and understanding the above detailed description. It is intended that the invention be construed as including all such modifications and alterations insofar as they come within the scope of the appended claims or the equivalents thereof.

Having thus described the preferred embodiments of the present invention, we now claim:

1. An implantable cuff electrode for encircling internal body tissues, the cuff comprising:

a self-curling sheet of a first material which includes: i) a first resiliently extensible elongate layer defining a first longitudinal axis; and, ii) a second elongate layer bonded to the first layer and holding an interface therebetween extended, the first layer being biased by resilient contractive forces acting in a direction oblique to said first longitudinal axis to curl the sheet into a helix; and, at least one conductive segment disposed on an interiorly defined periphery of the helix.

2. The implantable cuff electrode according to claim 1 wherein said first material is non-conductive.

3. The implantable cuff electrode according to claim 2 further comprising a plurality of conductive segments disposed along said first longitudinal axis.

4. The implantable cuff electrode according to claim 3 wherein each of said plurality of conductive segments are electrically conductive and further including an electrically conductive lead being connected to and extending from each of said plurality of conductive segments.

5. The implantable cuff electrode according to claim 4 wherein each of said plurality of conductive segments includes a contact member electrically connected to a one of said electrically conductive leads.

6. The implantable cuff electrode according to claim 5 wherein:

said electrically conductive leads extend from respective ones of said plurality of conductive segments along said first longitudinal axis forming a spine disposed on an exteriorly defined periphery of the helix; and, said first layer includes a plurality of apertures coincident with said plurality of conductive segments along said first longitudinal axis on said interiorly defined periphery of the helix.

7. The implantable cuff electrode according to claim 6 wherein said second elongate layer defines a second longitudinal axis coincident with said first longitudinal axis.

8. A cuff electrode for helically encircling internal body tissues, the cuff comprising:

a first resiliently biased elongate sheet defining a first longitudinal axis;

a second resiliently biased elongate sheet defining a second longitudinal axis substantially in parallel with said first longitudinal axis;

a bonding layer connecting said first sheet to said second sheet for holding a stiff interface therebetween, whereby biasing forces of the first sheet combine with biasing forces of the second sheet through said bonding layer resulting in a sum force oblique to a one of said first and second longitudinal axes urging the cuff to curl into a helix; and, at least one conductive segment disposed on an interiorly defined periphery of said helix.

9. A nerve cuff electrode for helically engaging body tissue comprising:

a laminate sheet biased to curl into a helix; and, at least one conductive member disposed on an interiorly defined periphery of said sheet.

10. The nerve cuff electrode according to claim 9 wherein said at least one conductive member is electrically conductive.

11. The nerve cuff electrode according to claim 10 wherein said at least one conductive member includes a contact surface adapted for recording electrical activity in said body tissue.

12. The nerve cuff electrode according to claim 10 wherein said at least one conductive member includes a contact surface adapted for stimulating electrical activity in said body tissue.

13. The nerve cuff electrode according to claim 9 wherein said at least one conductive member is fluid conductive.

14. The nerve cuff electrode according to claim 9 wherein said at least one conductive member includes an electrically conductive member and a fluid conductive member.

15. The nerve cuff electrode according to claim 14 wherein said electrically conductive member includes a contact surface adapted for recording electrical activity in said body tissue.

16. The nerve cuff electrode according to claim 14 wherein said electrically conductive member includes a contact surface adapted for stimulating electrical activity in said body tissue.

17. The nerve cuff electrode according to claim 9 wherein said laminate sheet includes stressed and unstressed polymer laminates.

18. The nerve cuff electrode according to claim 9 wherein said at least one conductive member includes:

an electrically conductive contact member adapted to engage a nerve encircled by said nerve cuff electrode; and, an electrically conductive lead on said laminate sheet connected to and extending from the contact member.

19. The nerve cuff electrode according to claim 18 wherein said electrically conductive lead is disposed in said laminate sheet.

20. A cuff electrode for helically encircling body tissues, the cuff comprising:

a first resiliently biased elongate sheet defining a first longitudinal axis;

a second resiliently biased elongate sheet defining a second longitudinal axis substantially in parallel with said first longitudinal axis, the second sheet being bonded to said first sheet and holding a stiff interface therebetween, whereby biasing forces of the first sheet combine with biasing forces of the second sheet resulting in a sum force oblique to a one of said first and second longitudinal axes urging the cuff electrode to curl into a helix; and, at least one conductive segment disposed on an interiorly defined periphery of the helix.

21. The cuff electrode according to claim 20 wherein said at least one conductive segment is electrically conductive.

22. The cuff electrode according to claim 21 wherein said at least one conductive segment includes a contact surface adapted for recording electrical activity in a nerve.

23. The cuff electrode according to claim 21 wherein said at least one conductive segment includes a contact surface adapted for stimulating electrical activity in a nerve.

24. The cuff electrode according to claim 21 wherein said at least one conductive segment is fluid conductive.

25. The cuff electrode according to claim 20 wherein said at least one conductive segment is fluid conductive.

* * * * *